(12) United States Patent
Ravenscroft et al.

(10) Patent No.: US 10,820,981 B2
(45) Date of Patent: Nov. 3, 2020

(54) SURGICAL TOOLS AND JOINT KINEMATIC RECONSTRUCTION TECHNIQUES

(71) Applicant: Arthrex, Inc., Naples, FL (US)

(72) Inventors: Matthew Ravenscroft, Mere (GB); Reinhold Schmieding, Naples, FL (US); Thomas Dooney, Jr., Naples, FL (US); Peter Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 185 days.

(21) Appl. No.: 15/973,470

(22) Filed: May 7, 2018

(65) Prior Publication Data
US 2019/0336261 A1   Nov. 7, 2019

(51) Int. Cl.
| | | |
|---|---|---|
| A61F 2/00 | (2006.01) |
| A61B 17/04 | (2006.01) |
| A61B 17/06 | (2006.01) |
| A61F 2/46 | (2006.01) |

(52) U.S. Cl.
CPC ........ A61F 2/0063 (2013.01); A61B 17/0482 (2013.01); A61B 17/06166 (2013.01); A61F 2/4612 (2013.01); A61F 2/4603 (2013.01); A61F 2002/0072 (2013.01); A61F 2002/4627 (2013.01)

(58) Field of Classification Search
CPC .. A61F 2/00; A61F 2/0063; A61F 2/46; A61F 2/4612; A61B 17/04; A61B 17/0482; A61B 17/06
See application file for complete search history.

(56) References Cited

U.S. PATENT DOCUMENTS

| | | | |
|---|---|---|---|
| 6,723,041 B2 * | 4/2004 | Lau | A61B 17/00234 |
| | | | 600/37 |
| 8,585,773 B1 | 11/2013 | Kucklick | |
| 8,864,780 B2 | 10/2014 | Euteneuer et al. | |
| 9,005,224 B2 | 4/2015 | Euteneuer et al. | |
| 9,101,460 B2 | 8/2015 | Euteneuer et al. | |
| 9,113,977 B2 | 8/2015 | Euteneuer et al. | |
| 9,179,910 B2 | 11/2015 | Euteneuer et al. | |
| 9,179,961 B2 | 11/2015 | Euteneuer et al. | |
| 9,198,751 B2 | 12/2015 | Euteneuer et al. | |
| 9,314,331 B2 | 4/2016 | Euteneuer et al. | |
| 2003/0069467 A1 | 4/2003 | Lau et al. | |
| 2006/0009802 A1 * | 1/2006 | Modesitt | A61B 17/0057 |
| | | | 606/215 |
| 2009/0156986 A1 | 6/2009 | Trenhaile | |
| 2009/0156997 A1 | 6/2009 | Trenhaile | |
| 2011/0040311 A1 * | 2/2011 | Levin | A61B 17/0469 |
| | | | 606/151 |

(Continued)

OTHER PUBLICATIONS

International Search Report for International Application No. PCT/US19/30878 dated Aug. 20, 2019.

*Primary Examiner* — Christopher J Beccia
(74) *Attorney, Agent, or Firm* — Carlson, Gaskey & Olds, P.C.

(57) ABSTRACT

The disclosure relates to surgical tools and methods. The surgical tools can include a handle, a first rod extending from the handle, and a second rod extending from the handle. At least one of the first and second rods may be rotatable between a folded position and a spread position. The first and second rods may be closer together in the folded position than in the spread position.

17 Claims, 6 Drawing Sheets

(56) References Cited

U.S. PATENT DOCUMENTS

| | | | |
|---|---|---|---|
| 2012/0209401 A1* | 8/2012 | Euteneuer | A61F 2/0063 623/23.72 |
| 2015/0182326 A1 | 7/2015 | Euteneuer et al. | |
| 2015/0313705 A1 | 11/2015 | Euteneuer et al. | |
| 2015/0320543 A1 | 11/2015 | Zenz-Olson | |
| 2015/0327975 A1 | 11/2015 | Euteneuer et al. | |
| 2016/0030150 A1 | 2/2016 | Euteneuer et al. | |
| 2016/0030157 A1 | 2/2016 | Euteneuer et al. | |
| 2016/0058535 A1 | 3/2016 | Euteneuer et al. | |
| 2016/0256254 A1 | 9/2016 | Kucklick | |
| 2016/0256258 A1 | 9/2016 | Euteneuer et al. | |
| 2016/0262780 A1 | 9/2016 | Kucklick | |
| 2016/0324616 A1 | 11/2016 | Zenz-Olson et al. | |
| 2017/0150963 A1 | 6/2017 | Coleman | |
| 2017/0189164 A1 | 6/2017 | Zenz-Olson et al. | |

* cited by examiner

SURGICAL TOOLS AND JOINT KINEMATIC RECONSTRUCTION TECHNIQUES

BACKGROUND

This disclosure relates to surgical tools and assorted surgical techniques for improving the joint kinematics of an unstable joint.

Normal joint kinematics are achieved through balanced soft tissues that surround the articulating bones of a joint. An unstable joint can occur if there is significant disruption of the articulating bones or the surrounding soft tissues. Unstable joints can also occur within a replaced joint subsequent to an arthroplasty procedure. The resulting joint instability may cause pain, dysfunction, accelerated bone loss, soft tissue tears and premature arthritis.

SUMMARY

This disclosure relates to surgical tools and techniques. Surgical tools may include a handle and one or more rods extending from the handle. The surgical tools may be positionable between a folded position and a spread position. The techniques may be employed to reconstruct and/or improve the joint kinematics of any joint of the human musculoskeletal system.

A surgical tool according to an exemplary aspect of this disclosure may include, inter alia, a handle, a first rod extending from the handle, and a second rod extending from the handle. At least one of the first and second rods may be rotatable between a folded position and a spread position. The first and second rods may be closer together in the folded position than in the spread position.

A surgical tool according to an exemplary aspect of this disclosure may include, inter alia, a handle providing a first opening, a second opening, and a third opening. A first rod may extend from the handle and may be received in the first opening. A second rod may be selectively receivable in the second opening and in the third opening.

A surgical method of attaching a graft to a joint according to another exemplary aspect of this disclosure may include, inter alia, rolling a graft on a surgical tool outside of a joint space. A surgical tool may be inserted with the rolled graft through a portal. The graft may be unrolled by the surgical tool inside the joint space.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Figure 1:
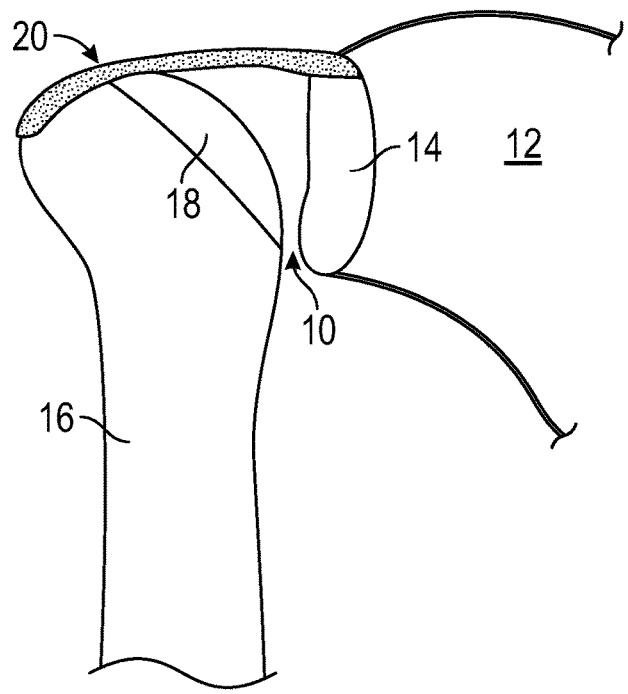
FIG. 1 illustrates a joint of a human musculoskeletal system.

FIG. 1 illustrates a joint 10 of the human musculoskeletal system. The joint 10 may be any joint of the musculoskeletal system of the human body. In one embodiment, the joint 10 is the glenohumeral joint of a shoulder. The joint 10 includes multiple bones including a scapula 12 and a humerus 16. Some of these bones articulate relative to one another. For example, the joint 10 includes a ball and socket joint formed between a head 18 of the humerus 16 and a glenoid 14, which is a cup-like recession of the scapula 12 configured to receive the head 18.

A capsule 20 generally covers the joint 10 and is surrounded and reinforced by various muscles, tendons and ligaments that are responsible for keeping the adjoining bones of the joint 10 together. The joint 10 may become unstable if there is significant disruption of the articulating bones (e.g., the humerus 16 and the glenoid 14), the capsule 20, or other surrounding muscles, tendons and/or ligaments. In one embodiment, the joint 10 could become unstable in response to a massive irreparable rotator cuff tear.

This disclosure describes joint kinematic reconstruction techniques for reconstructing an unstable joint, such as in response to a massive irreparable rotator cuff tear or other injury. Although joint kinematic reconstruction of a shoulder joint is described throughout this disclosure as one example joint kinematic reconstruction technique, this disclosure is not intended to be limited to shoulder reconstructions. In other words, the various techniques described herein may be employed to reconstruct and/or improve the joint kinematics of any joint of the human musculoskeletal system.

Figure 2:
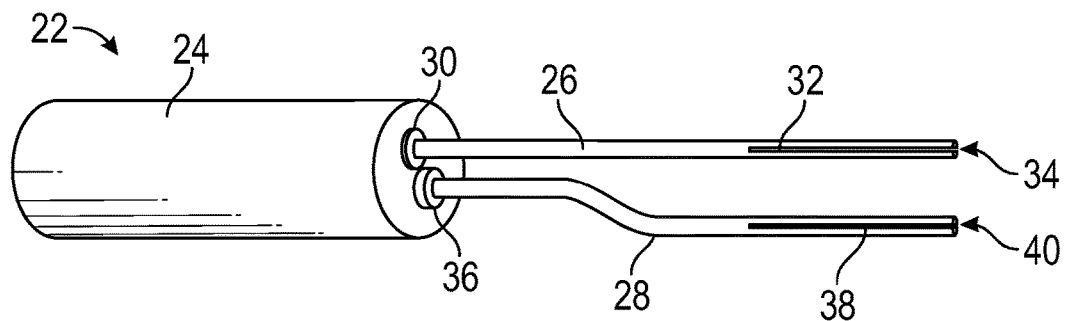
FIG. 2 illustrates an example surgical tool.

FIG. 2 illustrates an example surgical tool 22 that may be used in a surgical procedure, such as a joint kinematic reconstruction technique, for example. The surgical tool 22 includes a handle 24, and a first rod 26 and a second rod 28 extending from the handle 24. The example rod 26 is received in an opening 30 in the handle 24 and may include a slot 32 extending to its distal end 34 for receiving a graft (not shown). The rod 28 is received in an opening 36 in the handle spaced from the opening 30. The rod 28 may include a slot 38 extending to its distal end 40 for receiving a graft. In another embodiment, the slots 32, 38 do not extend to the distal end. Although slots 32, 38 are utilized in the example for receiving a graft, other attachment features, including those shown in FIGS. 9-10 in some examples, may be used for attaching a graft to the rods 26, 28.

Figure 3:
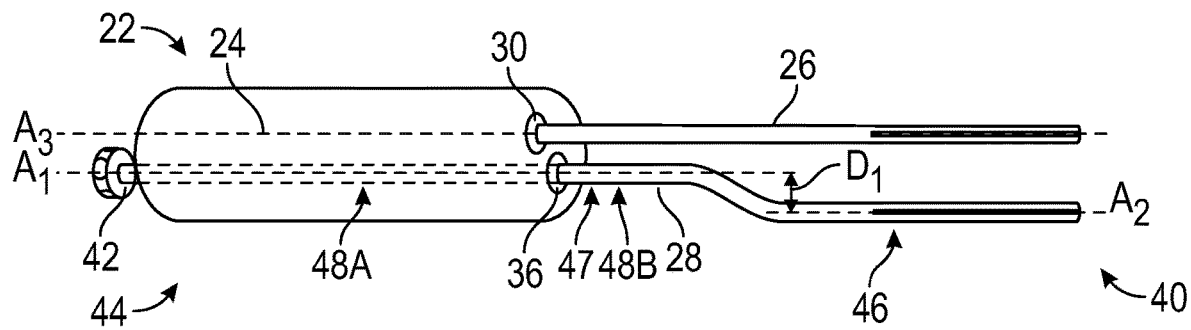
FIG. 3 illustrates the example surgical tool of FIG. 2.

FIG. 3 illustrates the example surgical tool 22 having the rod 28 extending along and rotatable within an axis A1, which extends through the opening 36 in the handle 24. The rod 28 may include a knob 42 near its proximal end portion 44 opposite the handle 24 from the distal end 40. The knob 42 may be manipulated to provide a rotational input to the rod 28. In the example surgical tool 22, the rod 26 is fixed; however, in other examples, both rods 26, 28 may be rotatable. One or both of the rods 26, 28 may be rotated for folding a graft received in the rods 26, 28 before shuttling the graft to a graft site, such as within a joint space, as is discussed further below. The graft may be folded using the surgical tool 22 for ease of insertion through an opening, one example being an arthroscopic portal, such as a cannula, during an arthroscopic procedure.

The rod 28 may include an offset portion 46 that is offset from a main portion 48, such that a central axis A2 extending through the offset portion 46 is spaced a distance D1 from the axis A1. The offset portion 46 may be distal of the main portion 48. However, other offset configurations are contemplated within the scope of this disclosure. In an example, the main portion 48 is rotatable about the axis A1 and includes a portion 48A received in the handle 24 and a portion 48B extending distally from the handle 24. The example rod 26 does not have an offset; however, in other examples, both the rods 26 and 28 may have an offset. The rod 26 extends along a central axis A3. Two or more of the axes A1, A2, and A3 may be substantially parallel in some examples, and, in the example shown, the axes A1, A2, and A3 are substantially parallel.

Figure 4:
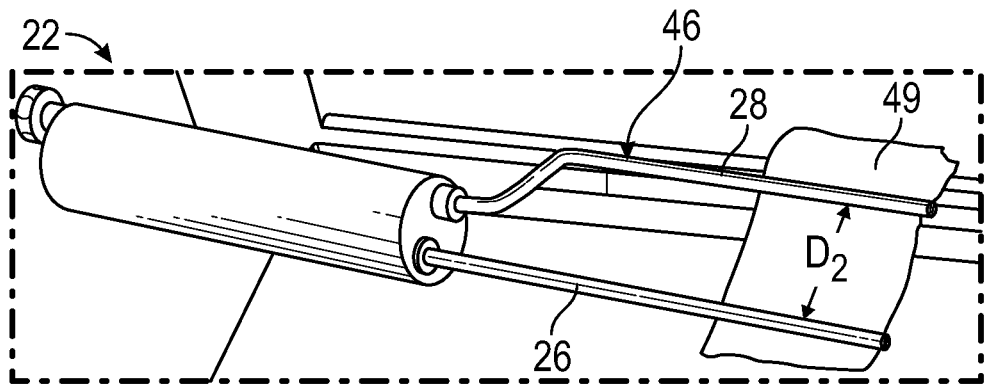
FIG. 4 illustrates the example surgical tool of FIGS. 2-3.

FIG. 4 illustrates a graft 49 received by the first rod 26 and the second rod 28 of the surgical tool 22. The surgical tool 22 and the graft 49 are shown in a spread position. In an example, in the spread position, the offset portion 46 of the rod 28 is its greatest distance D2 from the first rod 26, such that the coverage of the graft 49 with the rods 26, 28 is maximized. In some examples, the spread position of the graft 49 mimics the desired implanted position of the graft during a procedure. Utilizing one or more offsets allows the distance D2 to be greater than it would be without offsets, thus providing greater control and stability when shuttling and placing the graft 49 during a procedure.

The graft 49 could include either an allograft or an autograft. In one embodiment, the graft 49 is an acellular dermal extracellular matrix. ArthroFlex®, sold by Arthrex, Inc., is one type of graft 49 suitable for use to perform an exemplary joint kinematic reconstruction technique.

Figure 5:
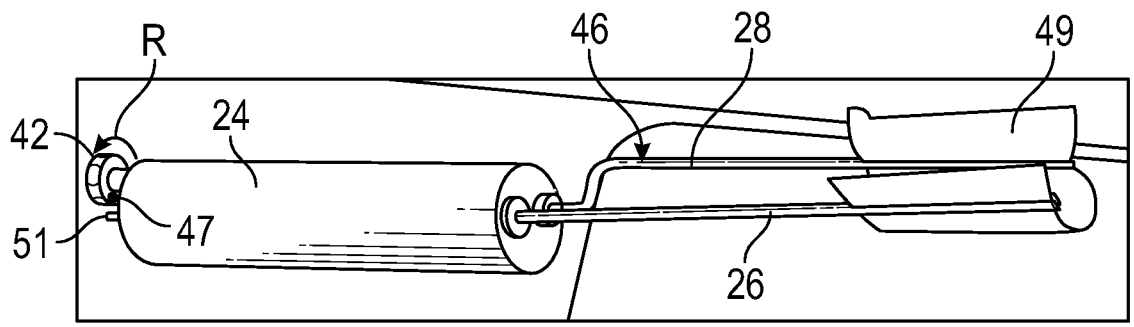
FIG. 5 illustrates the example surgical tool of FIGS. 2-4.

FIG. 5 illustrates the graft 49 received in a folded position in the first rod 26 and the second rod 28 of the surgical tool 22. The knob 42 may be rotated in the direction R to rotate the rod 28 from the spread position to the folded position. In the folded position, the offset portion 46 is closer to the first rod 26 than it is in the spread position shown in FIG. 4. In an example, the knob 42 may include one or more protrusions 47 and the handle 24 may include one or more protrusions 51 configured to interface with the protrusion 47 at a rotational limit, which could be set to any degree of rotation. In the folded position, the graft 49 and the rods 26, 28 are able to be shuttled through openings having a diameter or width smaller than the distance D2 (FIG. 4).

Figure 6:
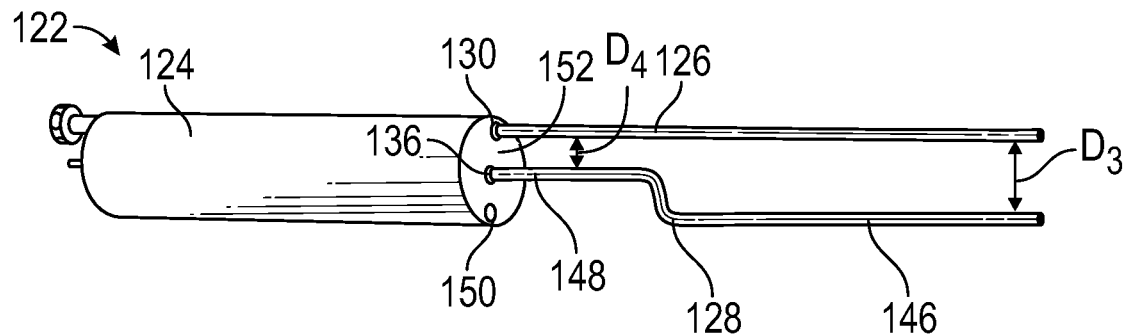
FIG. 6 illustrates another example surgical tool.

FIG. 6 illustrates another exemplary surgical tool 122. The surgical tool 122 is similar to the surgical tool 22, except that it includes a third opening 150 in the handle 124 for receiving the second rod 128. The first rod 126 may be fixed and received in an opening 130 in the handle 124; in other examples, the first rod 126 is rotatable in the opening 130. The second rod 128 may be receivable in the opening 136 as shown, or may be removed from the opening 136 and then inserted into the third opening 150. The positioning of the second rod 128 can be adjusted by providing openings 136 and 150 that can each receive the second rod 128. In some examples, this adjustability is based on a desired spread distance D3 between the offset portion 146 and the first rod 126, which is the maximum width between the offset portion 146 and the first rod 126 in the spread position. The actual spread distance D3 could be set at any dimension to accommodate different sized grafts. In some examples, the first rod 126 also includes an offset portion, and the distance D3 is the maximum width between offset portions of the first rod 126 and the second rod 128 in the spread position.

The adjustability may additionally or alternatively be based on a desired spread distance D4 between the main portion 148 and the first rod 126. The spread distance D4 is the maximum width between the first rod 126 and the main portion 148 of the second rod 128.

In the example shown, the second rod 128 has the offset; however, in other examples, the first rod 126 may alternatively have the offset, or both the first rod 126 and the second rod 128 may have an offset. In another example, a non-offset one of the rods 126, 128 is the removable and interchangeable rod.

Figure 7:
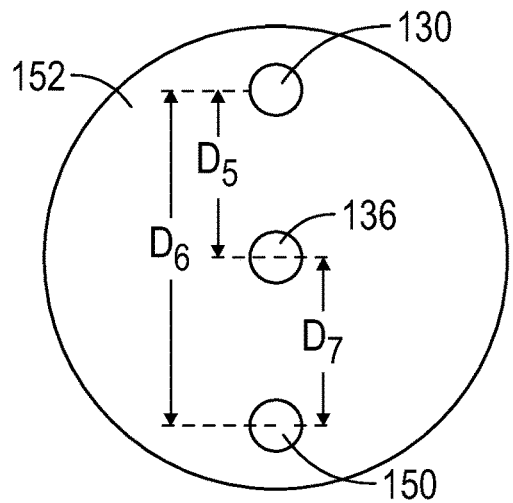
FIG. 7 illustrates a face of a handle of the example surgical tool of FIG. 6.

FIG. 7 illustrates an end view of the distal face 152 of the handle 124. The first rod 126 and second rod 128 are removed for FIG. 7 for ease of viewing. The center of the opening 130 and the center of the opening 136 are spaced apart by a distance D5. The center of the opening 130 and the center of the opening 150 are spaced apart a distance D6. The center of the opening 136 and the center of the opening 150 are spaced apart a distance D7. In an example, the distance D5 is different from the distance D6. In an example, the openings 130, 136, and 150 are aligned substantially linearly; however, non-linear arrangements of the openings 130, 136, and 150 may alternatively be utilized. In addition, although three openings are shown in the example, more than three openings may be used in other examples.

Figure 8:
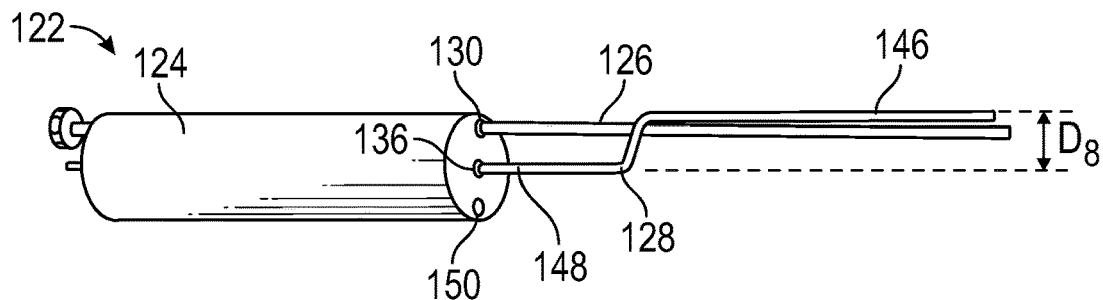
FIG. 8 illustrates the example surgical tool of FIGS. 6-7 in a folded position.

FIG. 8 illustrates the example surgical tool 122 in the folded position. As shown, in an example, a portion of the offset portion 146 may rotate beyond the first rod 126 in the folded position. In other examples, the offset portion 146 does not rotate beyond the first rod 126 in the folded position or rotates to be substantially aligned with the first rod 126. The adjustability of the surgical tool 122 may therefore additionally or alternatively be based on a desired spread distance D8 between the rods 126, 128 when positioned in the folded position. In the example shown, in which the offset portion 146 rotates beyond the first rod 126 in the folded position, the distance D8 is the maximum width of the main portion 148 and the offset portion 146 of the rod 128. The distance D8 may be selected based on the size of the arthroscopic portal to be used, among other factors.

Figure 9:
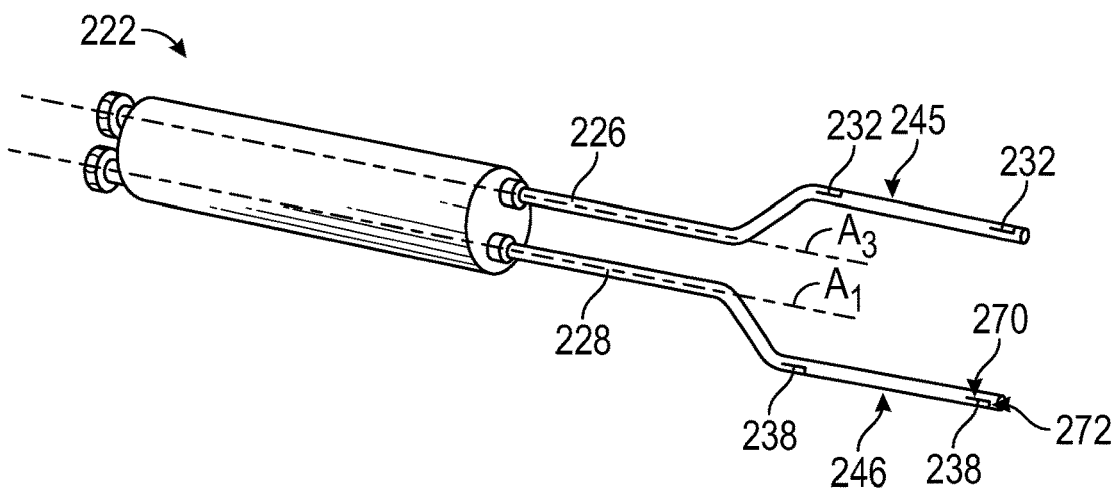
FIG. 9 illustrates another example surgical tool.

FIG. 9 illustrates an example surgical tool 222 in a spread position. In this example, the rod 226 is rotatable about the axis A3 and the rod 228 is rotatable about the axis A1. In some examples, both rods 226, 228 are rotatable between 0-90 degrees. In other examples, one of the rods 226, 228 may be fixed. In this example, the rod 226 includes an offset portion 245, and the rod 228 includes an offset portion 246. In other examples, only one of the rods 226, 228 includes an offset portion. The rod 226 includes suture slots 232, which may be provided at the offset portion 245. The rod 228 includes suture slots 238, which may be provided at the offset portion 246. In the example, each rod 226, 228 includes two suture slots 232, 238, but more or fewer suture slots may be utilized. The suture slots 232, 238 are configured to receive one or more suture strands, suture tape, any other suture-like product, or any thread-like material, which may be attached to a graft. In one example, sutures are attached at four corners of a graft and the sutures are received in the slots 232, 238.

Each suture slot 232, 238 may include an elongated portion 270 elongated along its respective rod 226, 228 and an access portion 272 transverse to the elongated portion 270 and extending to an outer surface of the respective rod 226, 228. In some examples, sutures are received in the rod 226, 228 through the access portion 272 and secured in the elongated portion 270.

Figure 10:
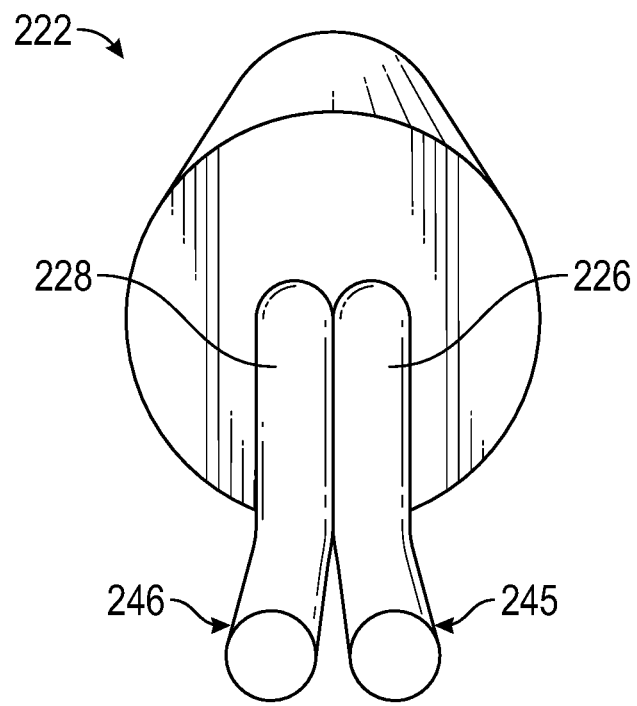
FIG. 10 illustrates the example surgical tool of FIG. 9 in a folded position.

FIG. 10 illustrates the example surgical tool 222 in a folded position. The rods 226, 228 are rotated such that the offset portions 245 and 246 are closer to one another than they were in a spread position.

The example surgical tools 22/122/222 may be utilized in joint kinematic reconstruction techniques. These techniques may include superior capsular reconstruction, for example. In other examples, the example surgical tools 22/122/222 may be utilized in any technique where a graft may be positioned against bone.

Figure 11:
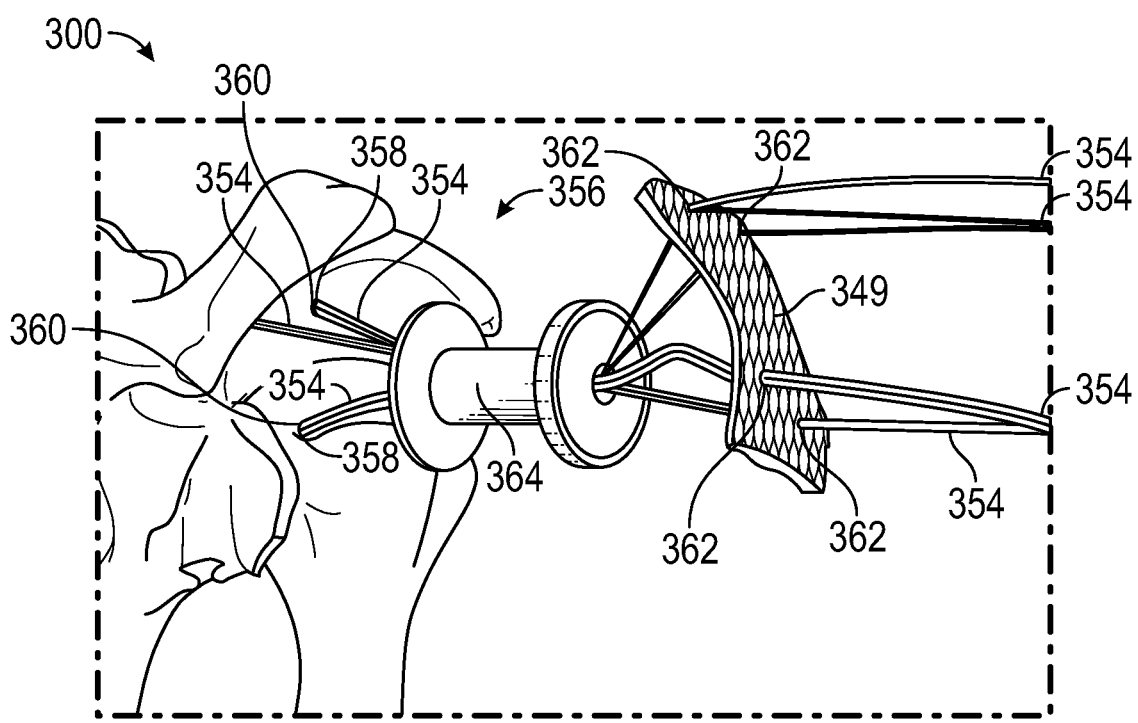
FIG. 11 schematically illustrates the retrieval and passage of multiple sutures through a graft.

As illustrated in FIG. 11, a surgeon may begin an example joint kinematic reconstruction technique 300 by selecting a desired positioning for fixating various sutures 354 inside a joint space 356. The fixation locations of the sutures 354 may be selected based on a surgeon's preference and are selected to best restore the joint kinematics of the joint being repaired. The sutures 354 may include individual suture strands, multiple suture strands, suture tape, any other suture-like product, or any thread-like material. The sutures 354 may be fixated inside the joint space 356 using various suture anchors 358. Holes 360 may optionally be pre-formed for receiving the suture anchors 358, such as with a drill, punch, and/or other tools (not shown) in some examples.

Any number of suture anchors 358 may be fixated inside the joint space 356 for attaching the sutures 354, and this disclosure is not limited to the specific number of suture anchors shown in this embodiment. The actual number of suture anchors 358 used is surgery-specific and may be quantified as the minimum number of suture anchors that is necessary to achieve graft fixation to the bone or bones of the unstable joint.

The graft 349 can be used to reconstruct an unstable joint. Holes 362 may be punched through the graft 349 that correspond with the spacing of the holes 360. The holes 362 are oriented and configured to accommodate the sutures 354 that are attached to the implanted suture anchors 358. The holes 362 permit the sutures 354 to slide relative to the graft 349 as the graft 349 is shuttled, pulled, maneuvered, or otherwise manipulated into place within a joint space 356.

As illustrated in FIG. 11, the graft 349 is first aligned and oriented at a location external to, or outside of, the joint space 356 in a manner that mimics its implanted position. Sutures 354, which have already been fixated inside the joint space 356, may then be retrieved from each implanted suture anchor 358 and pulled outwardly through a cannula 364 and then inserted through the graft 349 while the graft 349 is located outside of the joint space 356. Each hole 362 of the graft 349 is configured to accommodate one or more of the sutures 354. A person of ordinary skill in the art would be able to position the various arthroscopic portals required for performing an arthroscopic procedure. In another embodiment, the sutures 354 are retrieved from the joint space 356 one-by-one (i.e., sequentially), passed through the appropriate hole 362 of the graft 349, and then tensioned prior to shuttling an additional suture 354 through the cannula 364. In other embodiments, one or more sutures 354 may be passed through the graft 349 after the graft 349 is shuttled to the joint space 356.

Figure 12:
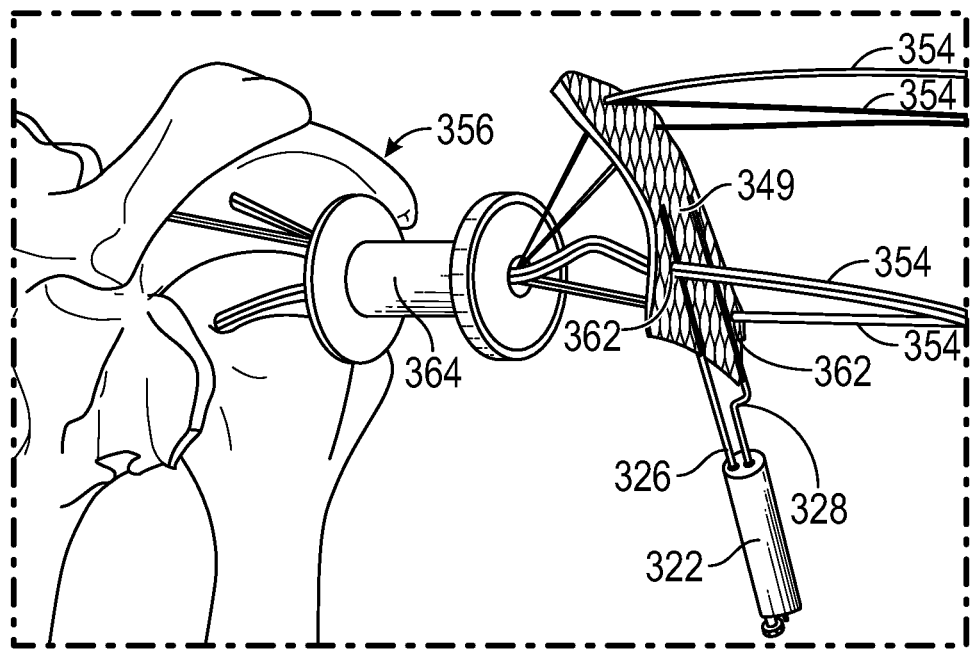
FIG. 12 schematically illustrates placement of the graft in an example surgical tool in the spread position.

FIG. 12 illustrates the surgical tool 322 receiving the graft 349 outside of the cannula 364 relative to the joint space 356. The surgical tool 322 is in the spread position and receives the graft 349 in its mimicked implanted position. In the example shown, the rods 326, 328 are placed internal to the openings 362 relative to the graft 349. In another example, the rods 326, 328 may be placed outside of the openings 362 relative to the graft 349. With reference to FIGS. 9-10, in some examples at this position, the sutures 354 passed through the graft 349 are received in suture openings in the rods 326, 328. With reference to the embodiment shown in FIGS. 6-8, in some examples, one of the first rod 326 and second rod 328 may be adjustable within openings in the handle 324 based on a desired spacing of the rods 326, 328 for dimensions of the graft 349 or the joint 356.

Figure 13:
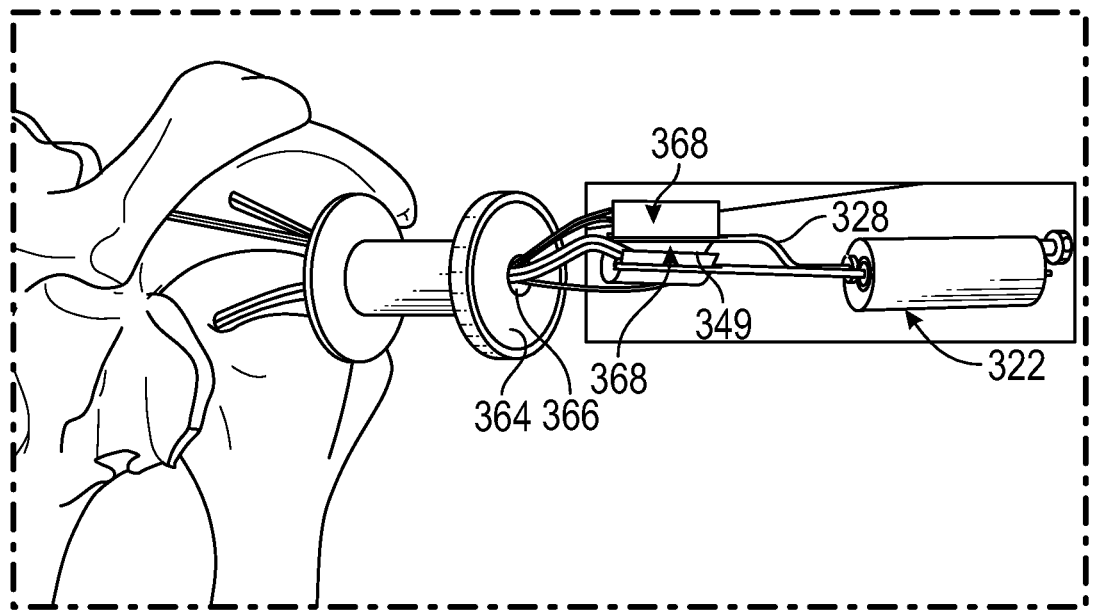
FIG. 13 schematically illustrates placement of the graft in the example surgical tool of FIG. 10 in the folded position.

FIG. 13 illustrates the surgical tool receiving the graft 349 outside of the cannula 364 relative to the joint space 356 and rotated into the folded position. The rod 328 is rotated, such that the surgical tool 322 and the graft 349 are in a folded position. In other examples, both rods 326 and 328 may be rotated, including in examples where one or both rods 326 and 328 have offset portions. In the folded position, the rods 326, 328 and the graft 349 are able to fit through the opening 366 in the cannula 364 for shuttling the graft 349 to the joint space 356. The graft 349 is therefore shuttled through the opening 366 to the joint space 356 in the folded position. In some examples, the surgeon may manually provide an additional fold to the ends 368 of the graft 349 prior to insertion.

Figure 14:
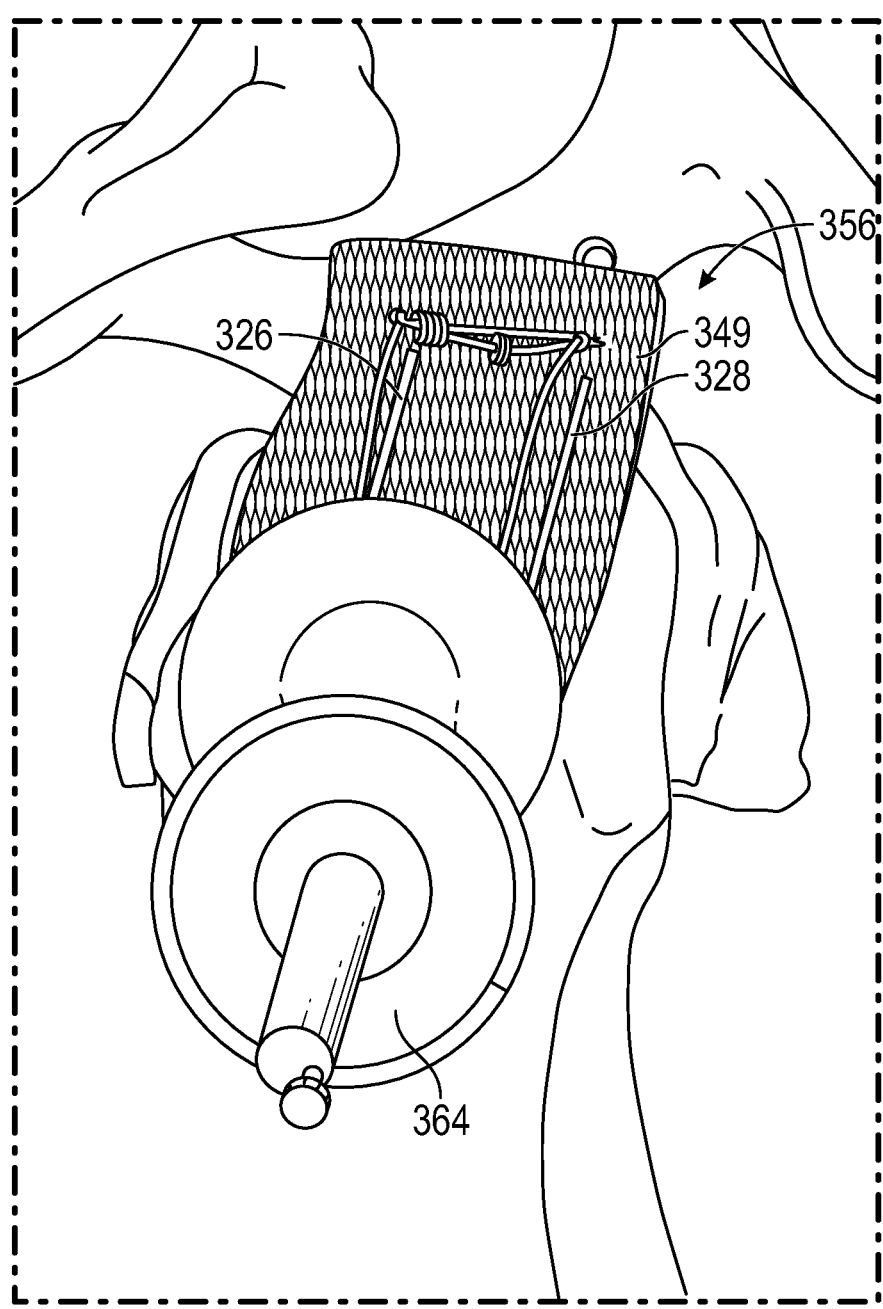
FIG. 14 schematically illustrate delivery of a graft into a joint space, with the graft and the surgical tool of FIG. 10 in the spread position.

FIG. 14 illustrates the graft 349 in the joint space 356 after being shuttled to the joint space 356. As shown, the surgical tool 322 is now rotated to the spread position, allowing the graft 349 to be placed in its implanted position. That is, after the rods 326 and 328 and the graft 349 are shuttled through the cannula 364, the rod 328 is rotated into the spread position to spread the graft 349 for placement in its implanted position. The rods 326, 328 may then be disengaged from the graft 349, such as, in some examples, by removing the graft 349 from slots (not shown) or the sutures 354 from suture slots (not shown) in the rods 326, 328. Tensioning of the sutures 354 may occur before and/or after disengagement of the rods 326, 328 for positioning the graft 349. The graft 349 may then be fixated to the bones of the joint.

Although the different embodiments are illustrated as having specific components, the embodiments of this disclosure are not limited to those particular combinations. It is possible to use some of the components or features from any of the embodiments in combination with features or components from any of the other embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical tool, comprising:
a handle;

a first rod extending from the handle and including a first suture slot configured for attachment of a graft to the first rod; and a second rod extending from the handle and including a second suture slot configured for attachment of the graft to the second rod, wherein at least one of the first and second rods is rotatable between a folded position and a spread position, and the first and second rods are closer together in the folded position than in the spread position.

2. The surgical tool as recited in claim 1, wherein the at least one of the first and second rod is rotatable about an axis through the second rod within the handle and includes a distal portion offset from a proximal portion.

3. The surgical tool as recited in claim 1, wherein each of the first rod and the second rod is rotatable.

4. The surgical tool as recited in claim 1, comprising a knob near a proximal end portion of the at least one of the first and second rods for rotating the at least one of the first and second rods.

5. The surgical tool as recited in claim 1, the first and second suture slots are each configured to receive a suture-like or thread-like material attached to the graft.

6. The surgical tool as recited in claim 1, wherein the first rod is fixed against rotation.

7. The surgical tool as recited in claim 6, wherein the second rod includes an offset, and the first rod is non-offset.

8. A surgical tool, comprising:
a handle;
a first rod extending from the handle and including a first slot configured to receive a graft and for attachment of the graft to the first rod; and
a second rod extending from the handle and including a second slot configured to receive the graft and for attachment of the graft to the second rod, wherein at least one of the first and second rods is rotatable between a folded position and a spread position, wherein the first and second rods are closer together in the folded position than in the spread position.

9. The surgical tool as recited in claim 8, wherein the first rod is fixed against rotation.

10. The surgical tool as recited in claim 9, wherein the second rod includes an offset, and the first rod is non-offset.

11. A surgical tool, comprising:
a handle;
a first rod extending from the handle and fixed against rotation; and
a second rod extending from the handle and rotatable between a folded position and a spread position, wherein the first and second rods are closer together in the folded position than in the spread position.

12. The surgical tool as recited in claim 11, wherein the second rod includes an offset, and the first rod is non-offset.

13. The surgical tool as recited in claim 12, wherein the first rod extends along a first axis, and the second rod extends along a second axis and a third axis different from the second axis, and at least two of the first, second, and third axes are substantially parallel to one another.

14. The surgical tool as recited in claim 13, wherein all of the first, second, and third axes are substantially parallel to one another.

15. The surgical tool as recited in claim 11, comprising a knob at a proximal end of the second rod for providing rotational input to the second rod.

16. The surgical tool as recited in claim 15, wherein the knob includes one or more first protrusions and the handle includes one or more second protrusions configured to interface with the one or more first protrusions at a rotational limit of the second rod.

17. The surgical tool as recited in claim 11, wherein the first rod includes a first opening for receiving a suture-like or thread-like material attached to a graft, and the second rod includes a second opening for receiving a suture-like or thread-like material attached to the graft.

\* \* \* \* \*